United States Patent [19]

Gross

[11] Patent Number: 5,042,981

[45] Date of Patent: Aug. 27, 1991

[54] ASSEMBLY COMPRISING A SURGICAL DRAPE AND A CONTOUR-TYPE ELECTROSURGICAL DISPERSIVE ELECTRODE, AND METHOD FOR ITS USE

[75] Inventor: Julio R. F. Gross, Palma De Mallorca, Spain

[73] Assignee: Fuchelman Sociedad Anonima, Spain

[21] Appl. No.: 346,781

[22] Filed: May 3, 1989

Related U.S. Application Data

[63] Continuation-in-part of Ser. No. 65,060, Jun. 19, 1987, abandoned.

[30] Foreign Application Priority Data

Jun. 25, 1986 [ES] Spain .................................... 556.589

[51] Int. Cl.⁵ ............................................. A61B 17/39
[52] U.S. Cl. ..................................... 606/32; 128/798; 128/852

[58] Field of Search .................. 606/32; 128/798, 802, 128/849, 852

[56] References Cited

U.S. PATENT DOCUMENTS 4,269,189 5/1981 Abraham ............................... 606/32
4,303,073 12/1981 Archibald ......................... 606/32 X Primary Examiner—Lee S. Cohen
Attorney, Agent, or Firm—Ostrolenk, Faber, Gerb & Soffen

[57] ABSTRACT

An assembly of a contour-type electrosurgical dispersive electrode and a surgical drape, the electrode having a contact surface with the skin in which its perimeter electrically and/or geometrically bounds a region of the surface of the body which contains the surgical field. The electrode is formed by one or more electrically conductive zones linked together conductively and/or capacitively.

31 Claims, 2 Drawing Sheets

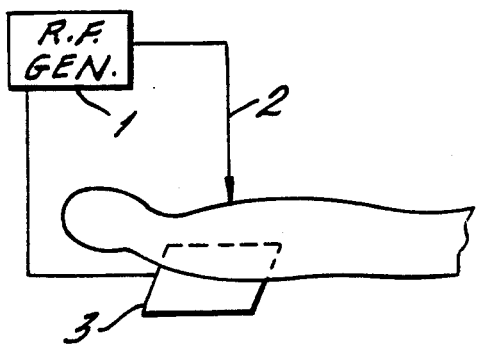
FIG._1. PRIOR ART
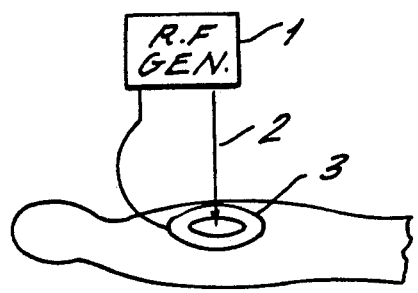
FIG._2.
FIG._3.
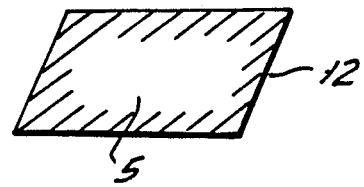
FIG._4. PRIOR ART
FIG._5.
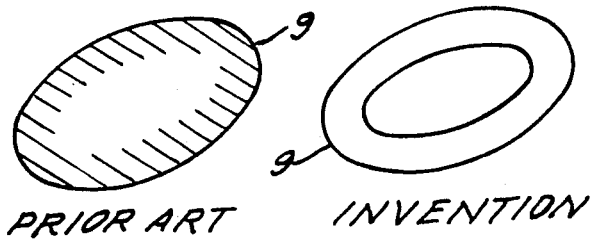
FIG._6.
PRIOR ART    INVENTION
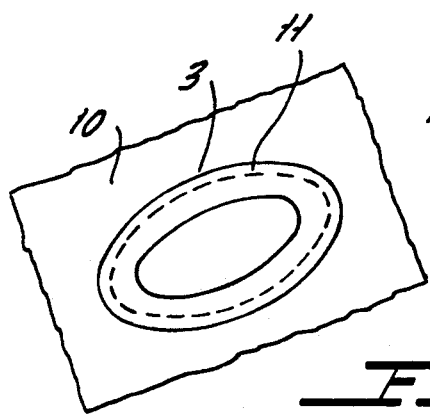
FIG._7.

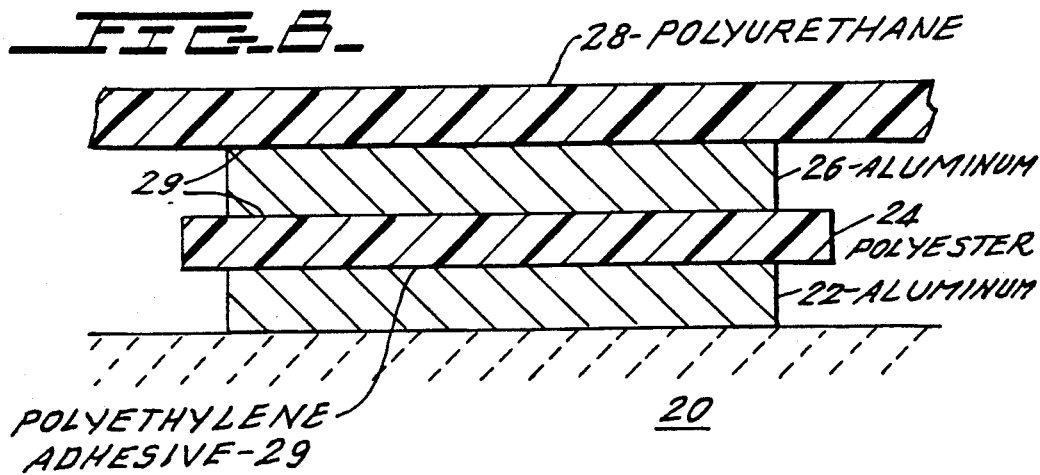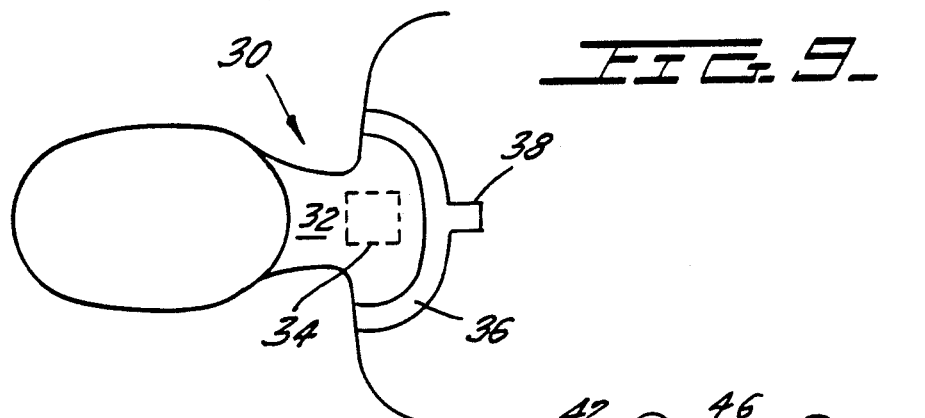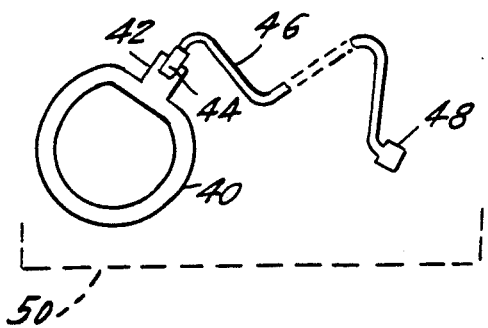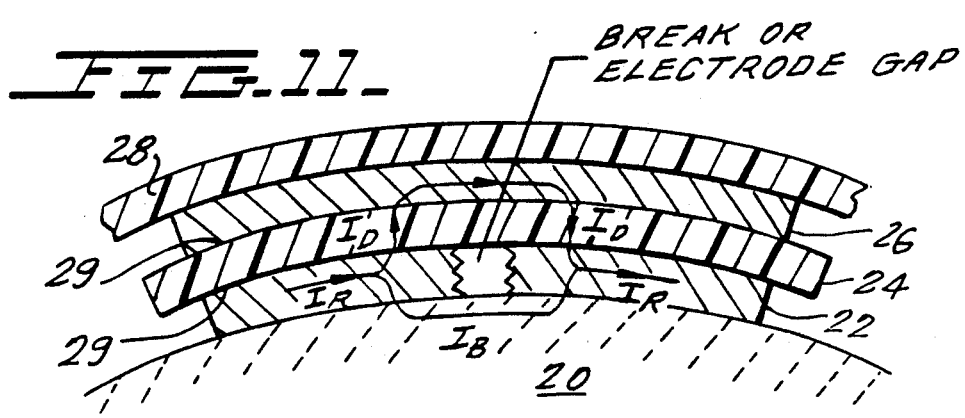

ASSEMBLY COMPRISING A SURGICAL DRAPE AND A CONTOUR-TYPE ELECTROSURGICAL DISPERSIVE ELECTRODE, AND METHOD FOR ITS USE

CROSS-REFERENCE TO RELATED APPLICATION

This is a continuation-in-part of U.S. Patent Application Ser. No. 65,060, filed June 19, 1987, now abandoned.

BACKGROUND OF THE INVENTION

The invention relates to an improvement in the electrosurgical electrode which is known as the dispersive, neutral or feedback electrode.

Referring to FIGS. 1 and 4, a known electrosurgical unit (ESU) comprises three main parts: a radiofrequency current (RFC) generator 1, an active electrode 2 and a neutral or dispersive electrode 3.

It is vital in electrosurgery to control the path followed by the current from the active electrode to the dispersive electrode to avoid hot spots that can injure the patient. Immediately at the active electrode there is a first "hot spot", which vaporizes the liquids in the tissue and breaks the tissue down. This, of course, is desirable, as it is the means for performing the electrosurgery. Other hot spots must be avoided. If the current is permitted to pass through the patient's body and concentrate at a localized point, for example where the patient's body contacts a grounded portion of the operating table, the patient can easily be seriously burned. The burn may go undetected because the patient is under anesthesia.

Such burns usually occur at a point where there is high pressure due to the patient's weight. This often occurs at a point where the patient contacts the operating table, or contacts a large plate-like dispersive electrode of the type which is placed under the patient's body. The pressure causes both reduced impedance and reduced cooling due to blood perfusion, whereby the local temperature can go high enough to destroy tissue. Necrosis caused by current leakage is often discovered long after the surgery.

RFC generators commonly employ a non-adjustable frequency of 2.2MHz, which is advantageous for cutting but also entails a great risk of burns at the dispersive electrode.

Various attempts have been made to control the current path by creating a minimum impedance path between the active electrode and the dispersive electrode. Previous solutions have attempted to use a large-area dispersive electrode beneath the patient, or to adhere the dispersive electrode to the patient's skin closer to the active electrode. None of these solutions has been fully successful.

On the one hand, wide-scale electrodes have proved unsatisfactory, because of the fundamental behavior of high-frequency currents. Until now the dispersive electrodes have been designed according to criteria selected to satisfy safety standards, for example, 1 square centimeter per 1.5 watts of radiofrequency power. However, such criteria are inadequate, because until now manufacturers have not taken into account that the RFC is not evenly distributed over the surface of the dispersive plate 5. On the contrary, as indicated by the cross-hatching in FIG. 4, almost all of the current is collected in about 20% of the electrode area, which is found in the peripheral zone 12 of the electrode in contact with the patient's skin. This edge effect can cause locally high current densities and hot spots.

On the other hand, a dispersive electrode on the patient's body close to the active electrode can physically interfere with the surgery, particularly since prior electrodes have been relatively thick, for example 1-2 mm. Surgeons prefer a large, clear surgical field because the surgery often expands unpredictably. For this reason, the known prior art has never succeeded in locating a dispersive electrode close to the surgical site.

One prior arrangement, disclosed in U.S. Pat. No. 4,269,189 to Abraham, includes a circular or oval electrode with a substantial central aperture. An adhesive layer contacts the patient's body both outside the periphery of the electrode and within the central aperture, for obtaining better adhesion. It is intended to be applied to any selected part of the patient's skin. However, this arrangement would interfere with the surgery if it were employed near the surgical field.

Theoretical and experimental studies carried out many years ago by Maxwell, Poisson, Laplace, and others, have shown that the most efficient electrode area for the collection of current from the active electrode is the peripheral portion of the dispersive electrode which is in contact with the patient's skin. See generally M. Aubry-Frize et al., "Assessment of Skin Temperature Elevation and Heat Diffusion with Electrosurgical Currents," *Medical Instrumentation*, Vol. 14, No. 5, at 272-275 (Sept.-Oct. 1980); J. D. Wiley et al., "Analysis and Control of the Current Distribution Under Circular Dispersive Electrodes," *Transac. on Biomedical Engineering*, Vol. BME-29, No. 5, at 381-85 (May 1982); and G. R. Newfeld et al., "Electrical Impedance Properties of the Body and the Problem of Alternate-Site Burns During Electrosurgery," *Medical Instrumentation*, Vol. 19, No. 2, at 83-87 (Mar.-Apr. 1985). The latter reference points out that burns can develop from excessive current density through the dispersive electrode as well as at alternate sites remote from either the active or the dispersive electrode.

These studies of the edge effect enabled Abraham to place a large aperture in the center of the electrode with an exposed adhesive pad therein. However, adhesive electrodes such as Abraham's are commonly used even farther from the surgical site than a plate electrode (under the patient) would be. Also, Abraham's electrode has the usual overall dimensions and shape of a standard electrode. Thus, Abraham's device is still subject to potential hot spots at its edges.

Other disadvantages of Abraham's device are that it covers the entire area with an adhesive pad and a gel pad and cannot breathe. It would physically interfere with the surgery if it were employed near the surgical field.

SUMMARY OF THE INVENTION

In view of the foregoing, a general object of the invention is to avoid the disadvantages of the prior art, by providing an improved electrosurgical dispersive electrode.

A more specific object is to provide a dispersive electrode which can control the electrosurgical current to avoid hot spots, preferably by reducing the current density, the length of the current path, or both.

A further object is to provide a dispersive electrode which can be located as close as possible to the surgical field, without interfering with the surgery if the surgical field must be enlarged.

A further object is to provide an electrode which can be disposed on the patient so as to surround the surgical site to the greatest extent possible, while remaining close to the site and not interfering with the surgery being performed.

Another object is to provide a biocompatible electrode, preferably made of a material that can breathe, and it should also be sterilizable.

Still another object is to provide a method of disposing an electrosurgical dispersive electrode around an operative site so as to provide a minimum current density, by surrounding the surgical site with the electrode to the greatest extent possible, while remaining close to the site and not interfering with the surgery being performed.

These and other objects are achieved by the invention, wherein a thin metallic electrode is adhered to the patient's skin at least partially surrounding the surgical field. Advantageous details of a layered structure of an assembly including the electrode and other associated metallic and nonmetallic layers are also disclosed hereinbelow.

The electrode of the assembly is strip-shaped, possibly forming a closed or open curve, such that it can be disposed surrounding or substantially surrounding the surgical site.

In the assembly, the electrode is preferably integrated with a biocompatible material such as a standard surgical drape. It can be adhered to the patient's skin such that the electrode is close to and at least partially surrounds the surgical site. Thus it performs the functions of both an electrode and a surgical drape, and can easily be cut with a scalpel if necessary.

This new development of collecting the radiofrequency current by means of a contour-type dispersive electrode, wherein substantially 100% of the skin contact area is active in the RFC collection, gives rise to the following advantages:

A. It minimizes RFC burns, as all the area which is taken into account when calculating the density of the current, is active (area 9) (see FIG. 6).

B. It minimizes the probability of interaction between the RFC of the ESU and other equipment which is also connected to the patient; e.g. anesthesia, cardiac monitors, etc.

C. It minimizes the probability of interaction between the biological processes of the body and the RFC, as the latter can only flow through a region which is substantially equal to the surgical area of the patient's skin which, containing the surgical incision, is bounded at the same time by the perimeter of the contour type dispersive electrode.

D. It can be easily and quickly disconnected.

E. It increases the safety of the surgeon and the surgical team as the spreading of the RFC is avoided.

F. Owing to its shape, it can have the maximum attainable proximity between the point of contact with the skin of the active electrode 2 and the dispersive electrode 9, whereby the impedance between these two electrodes is minimized, at the same time improving its performance and increasing the safety of the work carried out.

G. Because of its contour-type shape and film structure it can be fixed to the patient's skin bounding the aseptic surgical field, and for this reason it can be considered to be 100% radiotransparent, so in spite of its maximum proximity to the surgical site it does not cause any interference with the X-rays.

H. Because of its contour type-shape and its thinness, which is economical and flexible, it can be manufactured and applied as an integral product together with an adhesive membrane, such as surgical drape material, the latter acting as an adherent vehicle for the dispersive electrode and at the same time protecting the surgical zone from bacteria.

I. Because of its contour-type shape it can be manufactured with X-ray opaque lines that give radioscopic information about the boundary of the surgical field.

J. The prior art has avoided frequencies greater than about 0.5–2.2 MHz, because it was believed uncontrollable capacitive leakage currents would occur. With the invention, operation at least as high as 5 MHz and perhaps even 10 MHz or higher is feasible.

BRIEF DESCRIPTION OF THE DRAWINGS

Other objects, features and advantages of this invention will be understood from the following detailed description of embodiments thereof, in connection with the drawings, in which:

FIG. 1 is a schematic representation of a conventional electrosurgical unit includinq a dispersive electrode;

FIG. 2 is a schematic representation of an electrosurgical unit according to an embodiment of the invention, including a contour-type dispersive electrode;

FIG. 3 is a perspective view of the dispersive electrode in FIG. 2;

FIG. 4 is a perspective view of a conventional dispersive electrode, the functional peripheral area thereof being lined;

FIG. 5 is a perspective view of a contour-type dispersive electrode which includes more than one conductive region;

FIG. 6 is a comparative perspective view showing a conventional round-shaped dispersive electrode in comparison with the contour-type dispersive electrode of FIGS. 2 and 3;

FIG. 7 is a perspective view showing a contour-type dispersive electrode as in FIGS. 2 and 3, in combination with an adhesive membrane;

FIG. 8 is a cross-sectional view showing the detailed structure of the embodiment of FIG. 7;

FIG. 9 is a plan view of a further embodiment of the invention;

FIG. 10 is a perspective view showing another aspect of the invention; and

FIG. 11 is a view similar to FIG. 8, showing the conditions when a gap has formed in the layer 22.

DETAILED DESCRIPTION OF THE DISCLOSED EMBODIMENTS OF THE INVENTION

Referring now to FIGS. 2 and 3, there is seen a contour-type electrode 3, which is shaped so as to define an aperture in the center. Thus, it differs from the conventional type constituted by a simple connected surface, as shown at 5 in FIG. 4. In addition to providing a return path for the RFC, it limits the area through which the RFC flows to a region which is substantially equal to the area 6 of the patient's skin. The aperture is sized and located so as to surround the surgical incision line made by the active electrode 2 of the ESU, the surgical area 6 being bounded by the inside perimeter 4 of the contour-type dispersive electrode 3.

Taking into account the low penetration depth (skin effect) of the RFC in an electrically conductive material, this type of dispersive plate may be manufactured to a minimal thickness, thereby making it light, flexible and economical.

Because of its flexibility and light weight it can be fixed to the surface of the body by means of an adhesive material.

Contact with the skin can be conductive, capacitive, or a combination of both.

FIG. 5 shows an alternate embodiment of an electrode which is formed by a plurality of conductive zones 8 (here two), electrically linked together, either conductively or capacitively. Further capacitances can also be provided in one or both of the leads to the ESU.

Referring now to FIG. 7, according to a particularly preferred embodiment, the electrode 3 preferably comprises metal approximately 10-15 microns in thickness, preferably about 14.5 microns. The shape of the electrode 3 is selected such that the electrode is as close as possible to the active electrode 2 and surrounding it so as to define the maximum available angle of dispersion, given the geometry of the particular surgical site. The electrode is conductively coupled to the skin of the patient by direct contact. As discussed generally above, the current from the active electrode will travel mainly to the inner boundaries of the dispersive electrode; thus, the electrode may be made as narrow as possible. A width of 1-2 cm. is preferred. If the electrode is too narrow, the impedance will increase. Because of the "skin effect," as discussed previously, the current will flow through the tissues of the patient and primarily through the surface portions of the electrode; thus, the electrode may also be made as thin as possible, for flexibility and convenience. At a frequency of 1 megahertz, the skin depth has been found to be about 66 microns for copper and 85 microns for aluminum. However, experimentally an electrode thickness of about 14.5 microns has been found not to be too thin, while providing advantages due to its thinness and light weight.

The preferred material for the electrode 3 is aluminum, which is both nonallergenic and biocompatible. It is extremely ductile and malleable, so it can be formed thinly to provide the necessary flexibility. Aluminum less than about 0.5 mm thick is substantially X-ray transparent. Its electrical conductivity is high enough to provide a low contact impedance between the electrode 3 and the skin, but also is not too high.

The metal material should not have extremely high electrical conductivity. This avoids the development of "hot spots." It is undesirable to use stainless steel for the electrode 3, because this material is generally too rigid, even at these thicknesses.

Still referring to FIG. 7, the adhesive membrane 10 comprises a plastic layer approximately 25 microns in thickness. An adhesive material is disposed on the membrane 10 both within the electrode 3 and outside it, whereby the membrane 10 functions as a surgical drape. The combination of the membrane 10 and the electrode 3, being only about 39.5 microns thick in the example just described, or advantageously at most about 190 microns thick, and comprising extremely soft materials, can easily be cut by the surgeon if necessary, thus carrying out its advantageous functions without interfering with the surgical procedure.

Advantageously, the membrane 10 may comprise a commercially available surgical drape material of any well-known type. These materials "breathe" permitting both air and water vapor to pass through them to and from the patient's skin. At the same time, they are sterile and seal the skin, including the hair follicles, to prevent any bacteria from reaching the surgical site.

FIG. 8 is a cross-sectional view showing a particularly advantageous embodiment of the invention, namely a layered assembly comprising a series of laminated plastic and metallic layers. Disposed on the body 20 of the patient is, first, an aluminum layer 22 which comprises the electrode. This aluminum layer is substantially 14.5 microns in thickness. An electrical lead (not shown) is attached thereto by conventional means.

Disposed thereon is a layer 24, which may be made of polyester, cellulose acetate, or any other strong, biocompatible plastic. Desirably, it is approximately 23-100 microns in thickness, depending on the type of plastic. The thickness is determined according to the standards of the International Electrotechnical Commission, whose Standard IEC 601/2.2 requires the assembly to be strong enough to resist breaking when the cord is pulled under 4.5 kilograms of static force. In practice, a force of 5 kg can be withstood with this embodiment. These standards will also satisfy the requirements of the United States Food and Drug Administration.

A second aluminum layer 26, also about 14.5 microns thick, is disposed over the layer 24. If the layer 22 should be broken, a capacitive alternative current path through the layer 26 will still exist, coupled by displacement current, and will avoid all of the RFC being grounded through the patient along the break underneath the gap in the electrode. See FIG. 11.

In FIG. 11:

$I_R = I_D + I_B$;

$I_R$ = return electrode current;

$I_D$ = displacement current; and $I_B$ = body or patient current due to the break of layer 22.

Finally, overlaying the previously mentioned layers is a layer 28, which may be standard surgical drape material such as polyurethane, commonly about 25 microns in thickness. For manufacturing convenience and ease of working with the material, the thickness can be as high as, perhaps, 50 microns, but the thinner material is preferred because it is more compatible with the skin.

Preferably, a polyethylene, acrylic, or PTE (or Teflon), adhesive layer 29 is disposed between each two of the foregoing layers.

The adhesive layers 29 may be about 10 microns thick between the layers 22, 24 and 24, 26; and about 15 microns thick between the layers 26 and 28.

In connection with the foregoing, it should be noted that equivalent materials may be substituted for any of the above-mentioned layers. Also, the order of the layers can be changed. The adhesives can be modified or dispensed with if desired.

As thus constructed, an electrode assembly is provided which can be cut with a standard scalpel. It disperses current with a very low electrical impedance and avoids hot spots, leakage currents, and the other disadvantages of the prior art.

The shape of the electrode 3 (FIGS. 3 and 7) may be circular or oval for example, or any other geometry which is configured and dimensioned to surround the surgical site as closely as possible and surrounding it to great an angular extent as possible, while leaving enough space in the center to permit the surgeon the freedom of movement that is demanded according to medical practice.

As thus sized and shaped, the electrode provides a minimum impedance path between the active electrode and the RFC generator 1. This is accomplished, first, by providing the shortest possible path between the electrode 3 and the active electrode 2. Further improvement is obtained by surrounding the active electrode as much as possible to obtain the maximum possible dispersion of the current path.

As shown in FIG. 2, it is most preferable to accomplish this by providing a dispersive electrode 3 which completely surrounds the active electrode 2. However, in some surgery this is not easy.

FIG. 9 shows an example of a surgical site 34 in the neck area 32 of the patient 30. It is not easy to completely surround such a surgical site with an electrode. Accordingly, according to the invention, the dispersive electrode of this invention is configured in a U-shape, to provide well over 180° of coverage surrounding the surgical site, which provides very advantageous dispersion of the current path. The electrode may be manufactured with such curved shape. It may also be formed linearly or with some other shape, and then easily adapted to suit a given surgical area. A tab 38 extends from the electrode 36 for providing a convenient electrical connection.

In every case, the maximum angle of coverage surrounding the surgical site can be provided by an assembly according to the invention. Preferably, the electrode assemblies according to this invention are provided in a variety of standard sizes so that, for example, an extra-long electrode can be trimmed to provide the maximum surrounding coverage consistent with the geometry of the surgical site and the body of the patient.

According to a further advantageous aspect of the invention, as shown in FIG. 10, an electrode 40 may be provided with a tab 42. A connector 44 of a conventional type is provided for permanently connecting the tab 42 to a cable 46. A further connector 48 is provided for connection to external equipment. This embodiment is especially advantageous, in that the integral cable 46 and connector 48 are short enough to be packaged in a sterile package together with the electrode 40, but long enough to extend away from the surgical site, where a non-sterile cable can be attached to the connector 48. Desirably, the length of the cable 46 may be about 60 centimeters. The sterile packaging is indicated schematically at 50.

With reference to the aforementioned description, it is emphasized that the scope of the appended claims is not limited thereto, but rather that the disclosed embodiments of the invention can be modified without departing from the fundamental scope of the inventive principles disclosed herein.

What is claimed is:

1. An assembly for providing a dispersive radiofrequency current return path in an electrosurgical procedure, said assembly comprising:
   strip-shaped conductive electrode means shaped and sized for directly contacting the skin of the patient, adjacent to and at least partially surrounding a surgical field of said electrosurgical procedure; and
   surgical drape material bonded to one side of said electrode means, and shaped and sized so as to cover said surgical field.

2. An assembly as in claim 1, wherein said electrode means includes an electrode which is shaped so as to define an enclosed angle of at least 180° in order to at least partially surround said surgical field.

3. An assembly as in claim 2, wherein said electrode is U-shaped.

4. An assembly as in claim 2, wherein said electrode is shaped as a closed curve.

5. An assembly as in claim 1, wherein said electrode means comprises:
   a plurality of conductive zones; and
   capacitive means interconnecting said conductive zones for conducting radiofrequency current therebetween.

6. An assembly as in claim 1, wherein said electrode means comprises:
   a plurality of conductive zones; and
   conductive means interconnecting said conductive zones for conducting radiofrequency current therebetween.

7. An assembly as in claim 1, further comprising radiopaque means associated with said electrode means for radioscopically indicating the location of the surgical field.

8. An assembly as in claim 1, wherein an adhesive layer is disposed on said surgical drape material so as to adhere said assembly to said patient both within and outside said surgical field as defined by said electrode means.

9. An assembly as in claim 1, wherein said surgical drape material is polyurethane.

10. An assembly as in claim 9, wherein said surgical drape material is about 25–50 microns thick.

11. An assembly as in claim 1, wherein said electrode means includes an aluminum electrode.

12. An assembly as in claim 11, further comprising plastic strengthening means intermediate said electrode and said surgical drape material.

13. An assembly as in claim 12, wherein said strengthening means is a biocompatible plastic layer overlaying said electrode and about 23–100 microns thick.

14. An assembly as in claim 13, wherein said plastic layer is polyester.

15. An assembly as in claim 13, wherein said plastic layer is cellulose acetate.

16. An assembly as in claim 12, further comprising an aluminum auxiliary electrode intermediate said plastic strengthening means and said surgical drape material.

17. An assembly as in claim 16, wherein said electrode and said auxiliary electrode are both about 10–15 microns thick.

18. An assembly as in claim 16, further comprising an adhesive layer attached to said surgical drape material, said auxiliary electrode, said plastic strengthening means, and said electrode and adapted for being adhered to the skin of the patient.

19. An assembly as in claim 18, wherein said adhesive layer comprises polyethylene.

20. An assembly as in claim 18, wherein said adhesive layer comprises acrylic.

21. An assembly as in claim 1, wherein said assembly is at most about 190 microns thick.

22. An assembly as in claim 1, wherein said electrode means and said surgical drape material are constructed to be easily incisible by a standard scalpel.

23. In combination, an assembly as in claim 1, said assembly being sterile, and further comprising a sterile cable secured to said electrode means, said assembly and said cable being contained in package means for permitting said assembly and said cable to be vended while maintaining their sterility.

24. An electrosurgical method employing an active electrode and comprising the steps of:
   forming a scalpel-penetrable assembly which includes a thin strip-shaped dispersive electrode bonded to surgical drape material;
   defining the surgical field for a surgical procedure to be performed; and
   forming a low-impedance path from the active electrode to ground by grounding said dispersive electrode and adhering said assembly to the patient's skin with the electrode close to and at least partially surrounding the dispersive surgical field, and the surgical drape material covering the surgical field.

25. A method as in claim 24, which includes controlling the current distribution path within the patient's body so as to substantially avoid alternatesite burns and shock hazards.

26. A method as in claim 25, which includes limiting the current density at said dispersive electrode and substantially avoiding hot spots by disposing said dispersive electrode to define as large an angle surrounding the surgical field as possible in view of the location of the surgical field on the patient's body.

27. A method as in claim 26, further comprising a step of cutting said dispersive electrode and surgical drape material with a scalpel to permit further surgery to be performed in the region under the dispersive electrode.

28. An electrosurgical method employing an active electrode and comprising the steps of:
   forming a dispersive electrode assembly which includes a strip-shaped dispersive electrode and means for adhering said electrode to the body of a patient;
   defining a surgical field for a surgical procedure to be performed on the body of the patient; and
   forming a low-impedance path from the active electrode to ground by grounding said dispersive electrode and adhering said assembly to the patient's body with the dispersive electrode bounding said surgical field, while leaving the surgical field substantially unobstructed for surgery.

29. Electrosurgical equipment, comprising a circuit connection of:
   active electrode means operable for performing an electrosurgical procedure;
   an RF comprising means for supplying an RF current to said active electrode means; and
   dispersive electrode means for being adhered to the patient's body surrounding said surgical field, forming a low-impedance path from the active electrode means to said RF generator; and for bounding a surgical field for an electrosurgical procedure to be performed, while leaving the surgical field substantially unobstructed for surgery.

30. An electrosurgical dispersive electrode assembly comprising curved, strip-shaped conductive electrode means, shaped and sized for bounding a surgical field on the body of a patient, forming a low-impedance path from an active electrode to ground, while leaving the surgical field substantially unobstructed for surgery; and
   means for adhering said electrode means to said body of said patient.

31. An assembly as in claim 30, wherein said assembly further comprises surgical drape material adhered to one side of said curved conductive electrode means, which surgical drape material can cover the surgical field bounded by said conductive electrode means, said surgical field still remaining substantially unobstructive for surgery.

* * * * *